US008003399B2

(12) United States Patent
Song et al.

(10) Patent No.: US 8,003,399 B2
(45) Date of Patent: Aug. 23, 2011

(54) NITRITE DETECTION TECHNIQUE

(75) Inventors: Xuedong Song, Roswell, GA (US);
Rosann Marie Matthews Kaylor, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1030 days.

(21) Appl. No.: 11/217,099

(22) Filed: Aug. 31, 2005

(65) Prior Publication Data
US 2007/0048182 A1 Mar. 1, 2007

(51) Int. Cl.
*G01N 33/543* (2006.01)
*G01N 33/558* (2006.01)

(52) U.S. Cl. .......... 436/110; 436/514; 436/518; 422/56; 422/61; 435/5; 435/7.921

(58) Field of Classification Search .................. 436/110, 436/514, 518; 422/56, 61; 435/5, 7.92
See application file for complete search history.

(56) References Cited

U.S. PATENT DOCUMENTS

| | | | |
|---|---|---|---|
| 3,634,198 A | | 1/1972 | Truhan |
| 3,817,705 A | | 6/1974 | Stein et al. |
| 4,069,017 A | * | 1/1978 | Wu et al. .......... 436/97 |
| 4,299,917 A | | 11/1981 | Berger et al. |
| 4,434,235 A | | 2/1984 | Rabi et al. |
| 4,622,298 A | | 11/1986 | Mansour et al. |
| 4,631,255 A | | 12/1986 | Takino et al. |
| 4,637,979 A | | 1/1987 | Skjold et al. |
| 4,657,855 A | | 4/1987 | Corey et al. |
| 4,704,460 A | | 11/1987 | Corey |
| 4,742,011 A | | 5/1988 | Blake et al. |
| 4,743,560 A | | 5/1988 | Campbell et al. |
| 4,748,116 A | | 5/1988 | Simonsson et al. |
| 4,806,423 A | | 2/1989 | Hugl et al. |
| 4,814,271 A | | 3/1989 | Hugl et al. |
| 4,835,099 A | | 5/1989 | Mize et al. |
| 4,889,816 A | | 12/1989 | Davis et al. |
| 4,904,583 A | | 2/1990 | Mapes et al. |
| 4,920,046 A | | 4/1990 | McFarland et al. |
| 4,954,435 A | | 9/1990 | Krauth |
| 4,956,302 A | | 9/1990 | Gordon et al. |
| 4,978,625 A | | 12/1990 | Wagner et al. |

(Continued)

FOREIGN PATENT DOCUMENTS

EP 0698600 A1 2/1996

(Continued)

OTHER PUBLICATIONS

Abstract of Japanese Patent No. JP3210193, Sep. 13, 1991.

(Continued)

*Primary Examiner* — Krishnan S Menon
*Assistant Examiner* — Rebecca Fritchman
(74) *Attorney, Agent, or Firm* — Dority & Manning, P.A.

(57) ABSTRACT

A diagnostic test kit for detecting the presence or absence of nitrites within a test sample is provided. The test kit comprises an aromatic primary amine that is capable of reacting with a nitrite to form a diazonium ion. The test kit also comprises a lateral flow device that comprises a chromatographic medium and an absorbent material that receives the test sample after flowing through the chromatographic medium. The chromatographic medium defines a detection zone within which is contained a detection reagent (e.g., nucleophilic aromatic amine) that is capable of reacting with the diazonium ion to form an indicator (e.g., azo compound). The indicator exhibits a color that is different than the color of the detection reagent.

18 Claims, 1 Drawing Sheet

U.S. PATENT DOCUMENTS

| | | | |
|---|---|---|---|
| 4,980,298 | A | 12/1990 | Blake et al. |
| 5,073,340 | A | 12/1991 | Covington et al. |
| 5,075,077 | A | 12/1991 | Durley, III et al. |
| 5,075,078 | A | 12/1991 | Osikowicz et al. |
| 5,120,643 | A | 6/1992 | Ching et al. |
| 5,149,622 | A | 9/1992 | Brown et al. |
| 5,185,127 | A | 2/1993 | Vonk |
| 5,208,143 | A | 5/1993 | Henderson et al. |
| 5,252,459 | A | 10/1993 | Tarcha et al. |
| 5,275,785 | A | 1/1994 | May et al. |
| 5,415,994 | A | 5/1995 | Imrich et al. |
| 5,428,690 | A | 6/1995 | Bacus et al. |
| 5,464,739 | A | 11/1995 | Johnson et al. |
| 5,468,236 | A | 11/1995 | Everhart et al. |
| 5,512,450 | A | 4/1996 | Johnson et al. |
| 5,516,700 | A | 5/1996 | Smith et al. |
| 5,573,919 | A | 11/1996 | Kearns et al. |
| 5,591,645 | A | 1/1997 | Rosenstein |
| 5,602,040 | A | 2/1997 | May et al. |
| 5,610,077 | A | 3/1997 | Davis et al. |
| 5,622,871 | A | 4/1997 | May et al. |
| 5,656,503 | A | 8/1997 | May et al. |
| 5,663,044 | A | 9/1997 | Noffsinger et al. |
| 5,670,381 | A | 9/1997 | Jou et al. |
| 5,714,389 | A | 2/1998 | Charlton et al. |
| 5,750,359 | A | 5/1998 | Huh et al. |
| 5,759,860 | A * | 6/1998 | Smith et al. .................. 436/110 |
| 5,786,137 | A | 7/1998 | Diamond et al. |
| 5,788,863 | A | 8/1998 | Milunic |
| 5,798,273 | A | 8/1998 | Shuler et al. |
| 5,945,281 | A | 8/1999 | Prabhu |
| 5,989,924 | A | 11/1999 | Root et al. |
| 5,989,926 | A | 11/1999 | Badley et al. |
| 5,998,221 | A | 12/1999 | Malick et al. |
| 6,004,821 | A | 12/1999 | Levine et al. |
| 6,057,165 | A | 5/2000 | Mansour |
| 6,077,669 | A | 6/2000 | Little et al. |
| 6,124,107 | A | 9/2000 | Humes et al. |
| 6,130,100 | A | 10/2000 | Jobling et al. |
| 6,133,048 | A | 10/2000 | Penfold et al. |
| 6,156,271 | A | 12/2000 | May |
| 6,187,269 | B1 | 2/2001 | Lancesseru et al. |
| 6,194,220 | B1 | 2/2001 | Malick et al. |
| 6,194,221 | B1 | 2/2001 | Rehg et al. |
| 6,197,537 | B1 | 3/2001 | Rao et al. |
| 6,203,496 | B1 | 3/2001 | Gael et al. |
| 6,235,464 | B1 | 5/2001 | Henderson et al. |
| 6,274,324 | B1 | 8/2001 | Davis et al. |
| 6,294,391 | B1 | 9/2001 | Badley et al. |
| 6,352,862 | B1 | 3/2002 | Davis et al. |
| 6,399,398 | B1 | 6/2002 | Cunningham et al. |
| 6,485,926 | B2 | 11/2002 | Nemori et al. |
| 6,503,725 | B2 | 1/2003 | Huh |
| 6,514,769 | B2 | 2/2003 | Lee |
| 6,524,864 | B2 | 2/2003 | Fernandez de Castro |
| 6,528,652 | B1 | 3/2003 | Huh |
| 6,537,823 | B1 * | 3/2003 | Smith ........................... 436/125 |
| 6,573,108 | B1 | 6/2003 | Hardman et al. |
| 6,605,447 | B2 | 8/2003 | Weiss et al. |
| 6,627,459 | B1 | 9/2003 | Tung et al. |
| 6,653,149 | B1 | 11/2003 | Tung et al. |
| 6,669,908 | B2 | 12/2003 | Weyker et al. |
| RE38,430 | E | 2/2004 | Rosenstein |
| 6,689,618 | B1 | 2/2004 | Chen |
| 6,818,452 | B2 | 11/2004 | Wong |
| 6,875,185 | B2 | 4/2005 | Wong et al. |
| 6,951,631 | B1 | 10/2005 | Catt et al. |
| 6,951,730 | B2 | 10/2005 | Small et al. |
| 6,979,576 | B1 | 12/2005 | Cheng et al. |
| 7,044,919 | B1 | 5/2006 | Catt et al. |
| 7,052,831 | B2 | 5/2006 | Fletcher et al. |
| 2002/0042149 | A1 | 4/2002 | Butlin et al. |
| 2002/0045273 | A1 | 4/2002 | Butlin et al. |
| 2002/0137117 | A1 | 9/2002 | Small et al. |
| 2003/0124739 | A1 | 7/2003 | Song et al. |
| 2004/0151632 | A1 | 8/2004 | Badley et al. |
| 2004/0161859 | A1 | 8/2004 | Guo et al. |
| 2005/0029924 | A1 | 2/2005 | Okay et al. |
| 2005/0036148 | A1 | 2/2005 | Phelan |
| 2005/0037510 | A1 | 2/2005 | Sharrock et al. |
| 2005/0109951 | A1 | 5/2005 | Fish et al. |
| 2005/0112085 | A1 | 5/2005 | MacDonald et al. |
| 2005/0112635 | A1 | 5/2005 | Gentle et al. |
| 2005/0112703 | A1 * | 5/2005 | Song .............................. 435/7.5 |
| 2005/0124072 | A1 | 6/2005 | Boga et al. |
| 2005/0191704 | A1 | 9/2005 | Boga et al. |
| 2005/0266579 | A1 * | 12/2005 | Mu et al. ........................ 436/97 |
| 2006/0003336 | A1 | 1/2006 | Song et al. |
| 2006/0127924 | A1 | 6/2006 | Hellyer et al. |

FOREIGN PATENT DOCUMENTS

| | | |
|---|---|---|
| WO | WO 9832018 A1 | 7/1998 |
| WO | WO 9927364 A1 | 6/1999 |
| WO | WO 0052464 A1 | 9/2000 |
| WO | WO 0062060 A2 | 10/2000 |
| WO | WO 0062060 A3 | 10/2000 |
| WO | WO 2004011906 A2 | 2/2004 |
| WO | WO 2004011906 A3 | 2/2004 |
| WO | WO 2005057214 A1 | 6/2005 |

OTHER PUBLICATIONS

Diavant Individual Test Areas from Roche Diagnostics, Inc., 2005, 2 pages.

Article—*Leukocyte esterase activity in effusion fluid or patients with otitis media*, Lebovics et al., Otolaryngology—Head and Neck Surgery, vol. 108, No. 3, 1993, pp. 248-250.

Search Report and Written Opinion for PCT/US2006/016907, Apr. 18, 2007.

Search Report and Written Opinion for PCT/US2006/011188, Sep. 4, 2006.

* cited by examiner

NITRITE DETECTION TECHNIQUE

BACKGROUND OF THE INVENTION

One of the most common bacterial infections is that of the urinary tract. Patients who need rapid diagnosis of urinary tract infections (UTIs) include premature newborn infants, prepubertal girls and young boys, sexually active women, elderly males and females, pre-operative patients, patients with chronic disease, patients with neurological disorders, patients with genitourinary congenital disorders including urethral valves and reflux, patients with sickle cell disease, patients with renal disease and polycystic kidney disease, patients having undergone renal transplantation and pregnant patients. The diagnosis of UTI in the elderly and in infants, in particular, is difficult because of different signs and symptoms and the inability to communicate.

One technique for diagnosing UTI involves measuring the level of nitrites in urine. In particular, many bacteria, such as *E. coli* (the most common bacterium causing urinary tract infection), contain an enzyme that reduces nitrate ions ($NO_3^-$) to nitrite ions ($NO_2^-$). Vesical urine of most healthy persons is free from bacteria and as such, the detection of nitrite in urine may be used to help diagnose urinary tract infection. Several methods have been developed for assessment of nitrites. For example, dipsticks based on detection of nitrites have been developed that contain an area predisposed with reagents. The test sample is spotted onto the area so that the nitrites react with the reagents, thereby inducing a color change. Unfortunately, such test methods generally require a controlled reading window. However, it is not always feasible to carefully monitor testing, particularly in consumer-based applications.

As such, a need currently exists for an improved technique for detecting an nitrites in a test sample.

SUMMARY OF THE INVENTION

In accordance with one embodiment of the present invention, a diagnostic test kit for detecting the presence or absence of nitrites within a test sample is disclosed. The test kit comprises an aromatic primary amine that is capable of reacting with a nitrite to form a diazonium ion. The test kit also comprises a lateral flow device that comprises a chromatographic medium and an absorbent material that receives the test sample after flowing through the chromatographic medium. The chromatographic medium defines a detection zone within which is contained a detection reagent (e.g., nucleophilic aromatic amine) that is capable of reacting with the diazonium ion to form an indicator (e.g., azo compound). The indicator exhibits a color that is different than the color of the detection reagent.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGURE in which.

Figure 1:
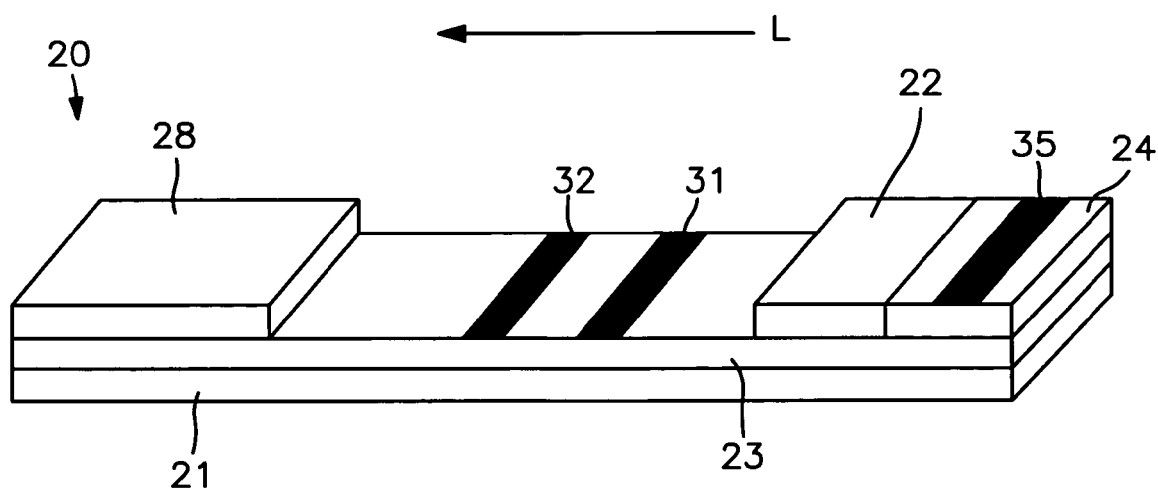
FIG. 1 is a perspective view of one embodiment of a lateral flow device that may be used in the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "test sample" generally refers to any material suspected of containing nitrites. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing nitrites may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the nitrites.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is directed to a device for detecting the presence of nitrites in a test sample. A variety of reagents are used to accomplish the detection of nitrites. For example, aromatic primary amines may be employed that have the ability to react with nitrite ions under certain conditions. Aromatic primary amines are amines in which at least one primary amino group is connected to an aromatic ring. Aromatic primary amines may, for instance, have the following formula:

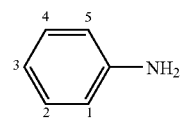

wherein positions 1 through 5 may be unsubstituted or substituted with a moiety, such as alkyl, alkylene, halogen, phenyl, hydroxyl, amino, amide, carboxyl, sulfonic, aromatic amine, aromatic amide, and other moieties. Particularly desired aromatic primary amines are those that are able to readily react with nitrite ions (or nitrous acid). Exemplary aromatic primary amines may include, for instance, aniline; 4-chloroaniline; 4-bromoaniline; 2,4,6-tribromoaniline; 2,4,6-trichloroaniline; α-trifluoro-m-toluidene; ortho-toluidine;

m- and p-aminophenol; ortho-tolidine; sulfanilamide, p-aminobenzoic acid; 1-amino-8-hydroxynaphthalene-3,6-disulphonic acid; aminoacetoanilide; aminophenyl ether, p-arsalinic acid; 4-amino-1-naphthalenecarbonitrile; derivatives thereof; and so forth.

As stated, the aromatic primary amine is generally capable of reacting with nitrite ions ("nitrites") under certain conditions. For instance, under acidic conditions, the nitrite ions form nitrous acid (nitric (III) acid), which has the formula $HNO_2$. Nitrous acid subsequently reacts with the aromatic primary amine to produce a diazonium ion having the following generic formula:

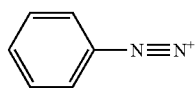

The diazonium ion may be zwitterionic in that the counterion of the diazonium moiety is covalently bound to the ring system. The ring system of the diazonium ion may be substituted or unsubstituted. Suitable diazonium salts that contain diazonium ions may include, for instance, diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; 4-diazo-3-hydroxy-7-[1,oxopropyl]-1-naphthylsulfonate; and derivatives thereof. Other suitable diazonium ions may be described in U.S. Pat. No. 4,637,979 to Skjold, et al.; U.S. Pat. No. 4,806,423 to Hugh, et al.; and U.S. Pat. No. 4,814,271 to Hugl, et al., which are incorporated herein in their entirety by reference thereto for all purposes. For instance, sulfanilamide ("SAA") may react with nitrous acid to form a diazonium ion as follows:

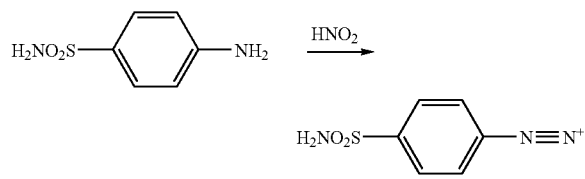

The resulting diazonium ion is an intermediate that is subsequently able to react with a detection reagent. Typically, the detection reagent is a nucleophilic (i.e., electron-rich) aromatic compound, such as a nucleophilic aromatic amine. Examples of such nucleophilic aromatic amines include, for instance, 8-hydroxyjulolidine, N,N-dimethylaniline; methylenedianiline; benzidine; benzoquinoline; aminoquinoline; m-phenylenediamine; α-trifluoro-m-toluidene; ortho-toluidine; m-aminophenol; ortho-tolidine; derivatives thereof; and so forth. One particularly suitable nucleophilic aromatic amine is N-1-naphthylethylene diamine ("NED"), which has the following structure:

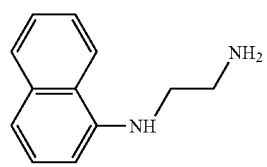

In some cases, it may be desirable to select the detection reagent based on its ability to be readily immobilized onto a solid substrate. In this regard, the present inventors have discovered that certain macromolecular reagents (e.g., polymers, oligomers, dendrimers, particles, etc.) may be particularly useful in the present invention. Generally speaking, such macromolecular reagents contain at least two functionalities, i.e., a reactive moiety and a macromolecular moiety, which are covalently or noncovalently joined. The macromolecular moiety may include, for instance, a polymeric moiety, such as a linear or branched, homopolymer or copolymer. The polymeric moieties may be natural, synthetic, or combinations thereof. Examples of natural polymeric moieties include, for instance, peptides, proteins, DNA/RNA and polysaccharides (e.g., glucose-based polymers). Examples of synthetic polymeric moieties include, instance, polyacrylic acid and polyvinyl alcohols. One particular example of a suitable polysaccharide detection reagent is activated dextran (polymeric moiety) conjugated to N-1-naphthylethylene diamine (aromatic amine moiety).

As indicated, the macromolecular moiety may also be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styrene-acrylic-vinyl terpolymer, polymethylmethacrylate, polyethylmethacrylate, styrene-maleic anhydride copolymer, polyvinylacetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns.

The particle may generally be joined to a reactive moiety using any of a variety of well-known techniques. For instance, covalent attachment of a particle to a substrate may be accomplished using carboxylic, amino, aldehyde, bromoacetyl, iodoacetyl, thiol, epoxy or other reactive functional groups, as well as residual free radicals and radical cations, through which a coupling reaction may be accomplished. A surface functional group may also be incorporated as a functionalized co-monomer because the surface of the particle may contain a relatively high surface concentration of polar groups. In certain cases, the particle may be capable of direct covalent bonding to a substrate without the need for further modification. It should also be understood that, besides covalent bonding, other attachment techniques, such as physical adsorption, may also be utilized in the present invention.

One particular technique for covalently bonding an aromatic amine reactive moiety to a particle will now be described in more detail. In this particular embodiment, the aromatic amine moiety is formed from N-(1-naphthyl)ethylenediamine ("NED"). The particle may be carboxylated latex particles available from Molecular Probes, Inc. or Bangs Laboratories, Inc. To covalently conjugate the particle with the aromatic amine, the carboxylic groups on the particle surface are first activated with a carbodiimide (e.g., ethylcarbodiimide hydrochloride (EDC)). Because NED possesses a primary amine group ($NH_2$), the activated carboxylic acid groups may then be reacted with the primary amine (—$NH_2$) group of NED to form an amide bond. This reaction may occur in a buffer, such as phosphate-buffered saline (PBS) (e.g., pH of 7.2), 2-(N-morpholino) ethane sulfonic acid (MES) (e.g., pH of 5.3), or borate buffer (e.g., pH of 8.5). If desired, the resulting detection reagent may then be blocked with ethanolamine, for instance, to block any remaining activated sites.

Regardless of the particular detection reagent selected, the intermediate compound formed by the initial nitrite reaction may subsequently react with the detection reagent to form an indicator having a different color. For example, a diazonium ion formed in the reaction between a nitrite and aromatic primary amine may electrophilically attack the nucleophilic or "electron-rich" ring system of a nucleophilic aromatic amine detection reagent. This reaction is often referred to as "coupling" and results in the formation of an aromatic azo indicator having the generic formula, R—N=N—R', wherein "R" and "R'" are aryl groups. In one embodiment, for example, a N-1-naphthylethylene diamine detection reagent reacts with a diazonium ion to form an azo indicator according to the following reaction:

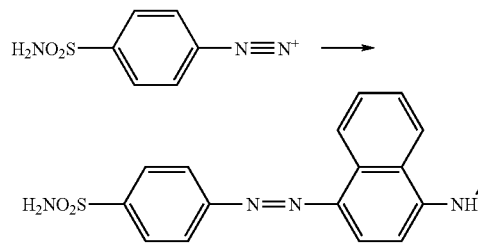

Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. Regardless, the absorption shift provides a color difference that is detectable, either visually or through instrumentation, to indicate the presence of nitrites within the test sample. For example, prior to contact with an infected test sample, the detection reagent may be colorless or it may possess a certain color. However, after reacting with the intermediate diazonium ion formed by the nitrite reaction described above, an aromatic azo indicator will form that exhibits a color that is different than the initial color of the detection reagent. Exemplary aromatic azo indicators that may be formed include dimethyldiazene, diphenydiazene, 1-naphthyl-2-naphthyl diazene, 3-chlorophenyl-4-chlorophenyl diazene, methylvinyl diazene, and 2-naphthylphenyl diazene.

As a result of the color change, the presence of nitrites in the test sample may be readily detected. The extent of the color change may be selectively controlled in accordance with the present invention to limit "false positives." More specifically, the aromatic amines may undergo an oxidation reaction if left in air or other oxidizing environment for too great a period of time. The resulting oxidized compounds may possess a certain color that indicates a "false positive" or at the very least, adversely affect the ability to semi-quantitatively or quantitatively determine the presence of the nitrites. Thus, the present inventors have discovered a technique for reducing the problem of such "false positives." Instead of simply measuring the results after a certain period of time, the desired reaction time may be achieved by selectively controlling the medium in which the reaction occurs. That is, the reaction medium is chromatographic in nature such that the reagents are allowed to flow in a consistent and controllable manner. While flowing through the medium, the aromatic primary amines and nitrites react to release a diazonium ion that subsequently couples with a nucleophilic aromatic amine detection reagent to form an aromatic azo compound. The aromatic azo indicator is immobilized within a discrete detection region for analysis. Due to the nature of the controlled fluid flow, any unreacted reagents travel to the end of the reaction medium so that they are unable to adversely interfere with observance of the aromatic azo compound in the detection region. Thus, to the extent that subsequent oxidation of aromatic compounds that are not captured at the detection region, the resulting color change will not occur within the detection region.

Various embodiments for accomplishing the detection of the nitrites using fluid flow control techniques will now be described in more detail. Referring to FIG. 1, for instance, one embodiment of a lateral flow device 20 that may be formed according to the present invention will now be described in more detail. As shown, the device 20 contains a chromatographic medium 23 optionally supported by a rigid support material 21. In general, the chromatographic medium 23 may be made from any of a variety of materials through which the test sample is capable of passing. For example, the chromatographic medium 23 may be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the chromatographic medium 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Likewise, the thickness of the membrane strip is generally small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the chromatographic medium 23. For example, the support 21 may be positioned directly adjacent to the chromatographic medium 23 as shown in FIG. 1, or one or more intervening layers may be positioned between the chromatographic medium 23 and the support 21. Regardless, the support 21 may generally be formed from any material able to carry the chromatographic medium 23. The support 21 may be formed from a material that is transmissive to light, such as transparent or optically diffuse (e.g., transluscent) materials. Also, it is generally desired that the support 21 is liquid-impermeable so that fluid flowing through the medium 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known in the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 20 also contains an absorbent material 28 that is positioned adjacent to the medium 23. The absorbent material 28 assists in promoting capillary action and fluid flow through the medium 23. In addition, the absorbent material 28 receives fluid that has migrated through the entire chromatographic medium 23 and thus draws any unreacted components away from the detection region to help reduce the likelihood of "false positives." Some suitable absorbent materials that may be used in the present invention include, but are not limited to, nitrocellulose, cellulosic materials, porous polyethylene pads, glass fiber filter paper, and so forth. The absorbent material may be wet or dry prior to being incorporated into the device. Pre-wetting may facilitate capillary flow for some fluids, but is not typically required. Also, as is well known in the art, the absorbent material may be treated with a surfactant to assist the wicking process.

To initiate the detection of nitrites within the test sample, a user may directly apply the test sample to a portion of the chromatographic medium 23 through which it may then travel in the direction illustrated by arrow "L" in FIG. 1. Alternatively, the test sample may first be applied to a sample application zone 24 that is in fluid communication with the chromatographic medium 23. The sample application zone 24 may be formed on the medium 23. Alternatively, as shown in FIG. 1, the sample application zone 24 may be formed by a separate material, such as a pad. Some suitable materials that may be used to form such sample pads include, but are not limited to, nitrocellulose, cellulose, porous polyethylene pads, and glass fiber filter paper. If desired, the sample application zone 24 may also contain one or more pretreatment reagents, either diffusively or non-diffusively attached thereto. In the illustrated embodiment, the test sample travels from the sample application zone 24 to a reagent zone 22 that is in communication with the sample application zone 24. As described above, the reagent zone 22 may be formed on the medium 23. Alternatively, as shown in FIG. 1, the reagent zone 22 is formed from a separate material or pad. Such a reagent pad may be formed from any material through which the test sample is capable of passing, such as glass fibers. To facilitate detection of nitrites in the manner described above, an aromatic primary amine is employed. In some embodiments, the aromatic primary amine may be mixed with the test sample prior to application to the device 20. Alternatively, the aromatic primary amine may be diffusively immobilized on the device 20 prior to application of the test sample. Such pre-application provides a variety of benefits, including the elimination of the need for a subsequent user to handle and mix the reagents with the test sample or a diluent. This is particularly useful in point-of-care applications when the user is not generally a trained lab technician or medical professional. The aromatic primary amine may be disposed downstream from the sample application zone 24. In this manner, the test sample is capable of mixing with the nitrites upon application. Alternatively, the aromatic primary amine may be positioned upstream from the sample application zone 24. For instance, a diluent may be employed to induce mixing between the aromatic primary amine and test sample.

If desired, the pH may be maintained at an acidic level to facilitate the desired nitrite reaction, such as described above. For instance, the pH is typically maintained at a level of less than about 6, and in some embodiments, from about 1 to about 4. To accomplish the desired pH level, a variety of techniques may be employed. For instance, an aromatic primary amine may be selected that is relatively acidic, such as p-arsalinic acid. Alternatively, an acidic pH modifier may be mixed with the aromatic primary amine prior to application to the device 20, mixed with the test sample, or both. The pH modifier may also be separately applied to the lateral flow device 20 so that it is capable of mixing with the reagents upon application to the test sample. Some examples of acidic pH modifiers that may be used in the present invention include, but are not limited to, mineral acids, sulfonic acids (e.g., 2-[N-morpholino] ethane sulfonic acid ("MES"), carboxylic acids, and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, acetic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid.

Referring again to FIG. 1, the lateral flow device 20 includes a detection zone 31 within which is immobilized a detection reagent (e.g., nucleophilic aromatic amine). The detection reagent may be applied directly to the medium 23 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. The amount of the detection reagent in the solution may range from about 0.001 to about 100 milligrams per milliliter of solvent, and in some embodiments, from about 0.1 to about 10 milligrams per milliliter of solvent. In one particular embodiment, the detection zone 31 is defined by the chromatographic medium 23 and formed by coating a solution thereon using well-known techniques and then dried. The detection reagent concentration may be selectively controlled to provide the desired level of detection sensitivity.

Typically, it is desired that the detection reagent be applied in a manner so that it does not substantially diffuse through the matrix of the chromatographic medium 23 (i.e., non-diffusively immobilized). This enables a user to readily detect the change in color that occurs upon reaction of the detection reagent with the intermediate diazonium ion. The detection reagent may form an ionic and/or covalent bond with functional groups present on the surface of the chromatographic medium 23 so that it remains immobilized thereon. For instance, a macromolecular moiety, such as described above, may facilitate the immobilization of the detection reagent at the detection zone 31.

One benefit of the lateral flow device of the present invention is its ability to readily incorporate one or more additional reagent zones to facilitate the above-described reaction. For example, referring again to FIG. 1, one such zone is a quenching zone 35. The quenching zone 35 is configured to remove compounds from the test sample that would otherwise interfere with the accuracy of the detection system. For example, contaminants (e.g., phenolics, bilirubin, urobilinogen, etc.) within the test sample may react with the intermediate diazonium ions to form aromatic azo compounds, thereby producing a "false negative" result. Thus, the quenching zone 35 may contain a quenching agent, such as a diazonium ion, that is capable of reacting with the reaction contaminants. Typically, the quenching agent is non-diffusively immobilized within the quenching zone 35 in the manner described above so that it does not flow through the medium 23 and interfere with testing. The location of the quenching zone 35 may vary, but is typically positioned upstream from the detection zone 31 and the reagent zone 22 to avoid interference with nitrite detection. For example, in the illustrated embodiment, the quenching zone 35 is positioned between the sample application zone 24 and the reagent zone 22. Alternatively, the quenching zone 35 may be positioned upstream from the sample application zone 24.

Another zone that may be employed in the lateral flow device 20 for improving detection accuracy is a control zone 32. The control zone 32 gives a signal to the user that the test is performing properly. More specifically, control reagents may be employed that flow through the chromatographic medium 23 upon contact with a sufficient volume of the test sample. These control reagents may then be observed, either visually or with an instrument, within the control zone 32. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If desired, the detectable substances may be disposed on particles such as described above. For example, latex particles may be utilized that are labeled with a fluorescent or colored dye. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

The location of the control zone 32 may vary based on the nature of the test being performed. In the illustrated embodiment, for example, the control zone 32 is defined by the chromatographic medium 23 and positioned downstream from the detection zone 31. In such embodiments, the control zone 32 may contain a material that is non-diffusively immobilized in the manner described above and forms a chemical and/or physical bond with the control reagents. When the control reagents contain latex particles, for instance, the control zone 32 may include a polyelectrolyte that binds to the particles. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 32 may simply be defined by a region of the absorbent material 28 to which the control reagents flow after traversing through the chromatographic medium 23.

Regardless of the particular control technique selected, the application of a sufficient volume of the test sample to the device 20 will cause a signal to form within the control zone 32, whether or not nitrites are present. Among the benefits provided by such a control zone is that the user is informed that a sufficient volume of test sample has been added without requiring careful measurement or calculation. This provides the ability to use the lateral flow device 20 without the need for externally controlling the reaction time, test sample volume, etc.

The detection zone 31, quenching zone 35, control zone 32, and any other zone employed in the lateral flow device 20 may generally provide any number of distinct detection regions so that a user may better determine the concentration of nitrites within the test sample. Each region may contain the same or different materials. For example, the zones may include two or more distinct regions (e.g., lines, dots, etc.). The regions may be disposed in the form of lines in a direction that is substantially perpendicular to the flow of the test sample through the device 20. Likewise, in some embodiments, the regions may be disposed in the form of lines in a direction that is substantially parallel to the flow of the test sample through the device 20.

One particular embodiment of a method for detecting the presence of nitrites within a test sample using the device 20 of FIG. 1 will now be described in more detail. Initially, a test sample containing nitrites is applied to the sample application zone 24 and travels in the direction "L" to the reagent zone 22. At the reagent zone 22, the nitrites are able to mix and react with the aromatic primary amines. As the mixture flows through the device 20, the nitrites and aromatic primary amines react further to form intermediate diazonium ions. The diazonium ions then flow to the detection zone 31 where they react with a nucleophilic aromatic amine detection reagent to form a colored azo indicator. After the reaction, the detection zone 31 changes color. Thus, the color or color intensity of the detection zone 31 may be determined, either visually or with instrumentation. If desired, the intensity of the color at the detection zone 31 may be measured to quantitatively or semi-quantitatively determine the level of nitrites present in the test sample. The intensity of the color at the detection zone 31 is typically directly proportional to nitrite concentration. The intensity of the detection signal "$I_s$" produced at the detection zone 31 may also be compared to a predetermined detection curve developed for a plurality of known nitrite concentrations. To determine the quantity of nitrites in an unknown test sample, the signal may simply be converted to nitrite concentration according to the detection curve. Regardless, the unreacted reagents travel past the detection zone 31 until they reach the absorbent material 28. In some cases, the aromatic compounds will self-react over a period of time in air to form colored compounds. However, because such colored compounds are not located at the detection region 31, they generally do not interfere with the detection accuracy.

The present invention provides a relatively simple, compact and cost-efficient device for accurately detecting the presence of nitrites within a test sample (e.g., urine). The test result may be visible so that it is readily observed by the person performing the test in a prompt manner and under test conditions conducive to highly reliable and consistent test results.

The present invention may be better understood with reference to the following examples.

EXAMPLE 1

Aromatic detection reagents were formed by dissolving 1.6 grams of dextran (molecular weight of 15,000, Sigma-Aldrich Chemical Co.) into 50 milliliters of water. 1.6 grams of sodium periodate ($NaIO_4$, Sigma-Aldrich Chemical Co.) in 50 milliliters of water was then added. The resulting solution was stirred overnight at room temperature and dialyzed in water three times. The solution was then dialyzed in 0.1M molar $NaHCO_3$. Dialysis was conducted using a Slide-A-Lyzer Dialysis Cassette tube (3.5K MWCO) obtained from Pierce Biotechnology, Inc. Thereafter, 0.8 grams of the activated dextran in 50 milliliters of sodium bicarbonate ($NaHCO_3$, 0.1 molar) containing 20% dimethyl sulfoxide ("DMSO") was combined with 0.3 grams of N-(1-naphthyl)ethylenediamine dihydrochloride ("NED-HCL"). The mixture was stirred for 1 hour and 0.4 grams of sodium cyanoborohydride ($NaBH_3CN$) was then added. The mixture was allowed to react overnight. Solid from the reaction mixture was collected and washed with acetone. The solid was dissolved in DMSO and precipitated in ethanol. The precipitate was centrifuged, air-dried, and dissolved in 0.1 N of HCl solution. Thereafter, the solution was dialyzed two times in 50-millimolar acetic acid solution. The resulting detection reagent was dextran N-(1-naphthyl)ethylenediamine ("DX-NED") and had a concentration of 5 milligrams per milliliter.

EXAMPLE 2

The ability to form a lateral flow device was demonstrated. An HF12002 nitrocellulose membrane laminated to a support card (Millipore, Inc.) was provided as the chromatographic medium. To form a detection zone, the DX-NED detection reagent of Example 1 (in 50 millimolar acetic acid solution) was striped onto the membrane. The membrane was dried for 1 hour at 37° C. A reagent pad was then fabricated from a glass fiber pad having a length of 10 centimeters (Millipore Inc.). More specifically, the pad was soaked with 1 milliliter of p-asalinic acid (10 milligrams per milliliter) and oxalic acid (20 milligrams per milliliter) in methanol. The glass fiber pad was then dried at 37° C. for 2 hours and laminated on one side of the membrane. A cellulose pad was laminated to the other side of the membrane card to provide an absorbent or wicking pad. A sample pad was then laminated to the glass fiber pad to provide a sample pad. The reagent pad and absorbent pad were in direct contact with the membrane, and the sample pad was in direct contact with the reagent pad. The fully assembled card was cut into 4-millimeter wide strip devices.

EXAMPLE 3

Lateral flow devices were formed as described in Example 2, except that the reagent pad was prepared by soaking the glass fiber pad with 1 milliliter of sulfanamide (20 milligrams per milliliter) and oxalic acid (80 milligrams per milliliter) in methanol.

EXAMPLE 4

Lateral flow devices were formed as described in Example 3, except that at a blue, water-soluble dye was striped onto the membrane near the wicking pad as a control zone.

EXAMPLE 5

The ability to detect the presence of nitrites in water was determined. Specifically, five (5) devices were formed as described in Example 2 and designated as Sample Nos. 1-5. 150 microliters of a nitrite solution of different concentrations in water (i.e., 0, 0.23, 0.46, 2.3, and 23 micrograms per milliliter) was directly applied to the sample pads of each sample, respectively. For Sample Nos. 4 and 5, a strong red color band developed on the detection zones within 1 minute of sample application. For Sample Nos. 2 and 3, a moderate red color band developed on the detection zones within about 2 minutes of sample application. Even after 30 minutes of sample application, no color band was formed on the detection zone of Sample No. 1.

EXAMPLE 6

The ability to detect the presence of nitrites in urine was determined. Specifically, eight (8) devices were formed as described in Example 3 and designated as Sample Nos. 1-8. 150 microliters of urine spiked with sodium nitrite solution of different concentrations in water (i.e., 0, 1, 2, 4, 8, 16, 32, and 64 micrograms per milliliter) was directly applied to the sample pads of each sample, respectively. For Sample Nos. 6-8, a strong red color band developed on the detection zones within 1 minute of sample application. For Sample Nos. 4 and 5, a moderate red color band developed on the detection zones within about 2 minutes of sample application. For Sample Nos. 2 and 3, a weak red color band developed on the detection zones within about 5 minutes of sample application. Even after 30 minutes of sample application, no color band was formed on the detection zone of Sample No. 1.

EXAMPLE 7

The ability to detect the presence of nitrites in urine was determined. Specifically, three (3) devices were formed as described in Example 4 and designated as Sample Nos. 1-3. 150 microliters of urine spiked with sodium nitrite solution of different concentrations in water (i.e., 0, 2, and 32 micrograms per milliliter) was directly applied to the sample pads of each sample, respectively. For Sample No. 3, a strong red color band developed on the detection zones within 1 minute of sample application. For Sample No. 2, a weak red color band developed on the detection zones within about 10 minutes of sample application. Even after 30 minutes of sample application, no color band was formed on the detection zone of Sample No. 1. In addition, a blue color was observed on the top of the wicking pad of each device after about ten minutes of sample application.

EXAMPLE 8

The ability to form particle-based detection reagents for use in a lateral flow device was demonstrated. 2 milliliters of poly(styrene-vinyl carboxylic acid) particles were washed with water and suspended in 2 milliliters of MES buffer (pH of 6.2). The particles were obtained from Bangs Laboratories, Inc. and had a size of 0.6 µm and a concentration of 10.2%. 200 milligrams of carbodiimide (in 2 milliliters of MES buffer) was added and the mixture was allowed to react for 0.5 hours. The mixture was then washed twice with borate buffer and suspended in 4 milliliters of dimethylformamide ("DMF") and 1 milliliter of borate buffer. 80 milligrams of N-(1-naphthyl)ethylenediamine dihydrochloride ("NED-HCl") in 1 milliliter of DMF containing 260 milligrams of NaOH was added to the particle suspension and reacted for 2 hrs. The mixture was then washed twice by borate buffer and once by water. The particles were then suspended in 5 milliliters of 0.2 molar acetic buffer.

EXAMPLE 9

Lateral flow devices were formed as described in Example 3, except that the particle-based detection reagent of Example 8 was striped onto the membrane to form the detection zone.

EXAMPLE 10

The ability to detect the presence of nitrites in urine was determined. Specifically, five (5) devices were formed as described in Example 9 and designated as Sample Nos. 1-5. 150 microliters of urine spiked with sodium nitrite solution of different concentrations in water (i.e., 0, 2, 8, 32 and 64 micrograms per milliliter) was directly applied to the sample pads of each sample, respectively. For Sample Nos. 4 and 5, a strong red color band developed on the detection zones within 1 minute of sample application. For Sample No. 3, a moderate red color band developed on the detection zone within about 2 minutes of sample application. For Sample No. 2, a weak red color band developed on the detection zone within about 5 minutes of sample application. Even after 30 minutes of sample application, no color band was formed on the detection zone of Sample No. 1.

EXAMPLE 11

Lateral flow devices were formed as described in Example 2, except that the detection zone was formed by striping the HF12002 nitrocellulose membrane with NED-HCl.

EXAMPLE 12

The ability to detect the presence of nitrites in water was determined. Specifically, five (5) devices were formed as described in Example 11 and designated as Sample Nos. 1-5. 150 microliters of a nitrite solution of different concentrations in water (i.e., 0, 0.23, 0.46, 2.3, and 23 micrograms per milliliter) was directly applied to the sample pads of each sample, respectively. For Sample Nos. 4 and 5, a strong red color band developed on the detection zones within 1 minute of sample application. For Sample Nos. 2 and 3, a moderate red color band developed on the detection zones within about 2 minutes of sample application. Even after 30 minutes of sample application, no color band was formed on the detection zone of Sample No. 1. However, significant diffusion of the colored dyes on membrane was observed.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A diagnostic test kit for detecting the presence or absence of nitrites within a urine test sample, the test kit comprising:
    a reagent pad on which an aromatic primary amine is disposed that is capable of reacting with a nitrite or nitrite derivative in the urine test sample to form a diazonium ion; and
    a lateral flow device that is in fluid communication with the reagent pad and comprises:
        a porous membrane defining a discrete detection zone that is separate and distinct from the reagent pad and within which is contained a nucleophilic aromatic amine detection reagent, the detection reagent being capable of reacting with the diazonium ion to form an azo indicator, the azo indicator exhibiting a color that is different than the color of the detection reagent; and
        an absorbent material that receives the urine test sample after flowing through the porous membrane.

2. The diagnostic test kit of claim 1, wherein the aromatic primary amine is p-arsalinic acid, sulfanilamide, or a derivative thereof.

3. The diagnostic test kit of claim 1, wherein the detection reagent comprises N-1-naphthylethylene diamine or a derivative thereof.

4. The diagnostic test kit of claim 1, wherein the detection reagent comprises a macromolecular moiety and an aromatic amine moiety.

5. The diagnostic test kit of claim 4, wherein the macromolecular moiety is formed from a polymer.

6. The diagnostic test kit of claim 5, wherein the polymer is a polysaccharide.

7. The diagnostic test kit of claim 4, wherein the macromolecular moiety is formed from a particle.

8. The diagnostic test kit of claim 4, wherein the aromatic amine moiety is formed from N-1-naphthylethylene diamine or a derivative thereof.

9. The diagnostic test kit of claim 1, wherein the aromatic primary amine is disposed on the lateral flow assay device.

10. The diagnostic test kit of claim 1, wherein the aromatic primary amine comprises aniline; 4-chloroaniline; 4-bromoaniline; 2,4,6-tribromoaniline; 2,4,6-trichloroaniline; α-trifluoro-m-toluidene; ortho-toluidine; m- and p-aminophenol; ortho-tolidine; sulfanilamide, p-aminobenzoic acid; 1-amino-8-hydroxynaphthalene-3, 6-disulphonic acid; aminoacetoanilide; aminophenyl ether, p-arsalinic acid; 4-amino-1-naphthalenecarbonitrile, or derivatives thereof.

11. The diagnostic test kit of claim 1, wherein the detection reagent comprises 8-hydroxyjulolidine, N,N-dimethylaniline; methylenedianiline; benzidine; benzoquinoline; aminoquinoline; m-phenylenediamine; α-trifluoro-m-toluidene; ortho-toluidine; m-aminophenol; ortho-tolidine; N-1-naphthylethylene diamine, or a derivative thereof.

12. The diagnostic test kit of claim 7, wherein the particle is a carboxylated latex particle.

13. The diagnostic test kit of claim 1, wherein the indicator is an aromatic azo compound.

14. The diagnostic test kit of claim 1, wherein the lateral flow device further comprises a sample pad configured to receive the test sample.

15. The diagnostic test kit of claim 14, wherein the sample pad also defines a quenching zone that contains an agent capable of reacting with a contaminant in the test sample.

16. The diagnostic test kit of claim 1, wherein the absorbent material includes nitrocellulose, a cellulosic material, a porous polyethylene pad, glass fiber filter paper, or a combination thereof.

17. The diagnostic test kit of claim 1, wherein the nitrite derivative is nitrous acid.

18. The diagnostic test kit of claim 1, wherein the detection zone is located laterally downstream from the reagent zone.

* * * * *